(12) United States Patent
Pramanick et al.

(10) Patent No.: US 11,865,206 B2
(45) Date of Patent: Jan. 9, 2024

(54) STABLE READY-TO-USE CARMUSTINE PHARMACEUTICAL COMPOSITION

(71) Applicant: EMCURE PHARMACEUTICALS LTD., Pune (IN)

(72) Inventors: Sougata Pramanick, Bhosari (IN); Aasiya Aslam Burhan, Bhosari (IN); Mukund Keshav Gurjar, Bhosari (IN); Hiren Pravinbhai Patel, Bhosari (IN); Deepak Pragjibhai Gondaliya, Bhosari (IN)

(73) Assignee: EMCURE PHARMACEUTICALS LTD, Pune (IN)

( * ) Notice: Subject to any disclaimer, the term of this patent is extended or adjusted under 35 U.S.C. 154(b) by 0 days.

(21) Appl. No.: 18/089,652

(22) Filed: Dec. 28, 2022

(65) Prior Publication Data

US 2023/0135144 A1    May 4, 2023

Related U.S. Application Data

(63) Continuation of application No. 17/268,022, filed as application No. PCT/IB2019/057404 on Sep. 3, 2019, now abandoned.

(30) Foreign Application Priority Data

Sep. 5, 2018  (IN) .............................. 201821033221

(51) Int. Cl.
| | | |
|---|---|---|
| C07D 471/04 | (2006.01) |
| A01N 43/90 | (2006.01) |
| A61K 9/00 | (2006.01) |
| A61K 31/175 | (2006.01) |
| A61K 47/26 | (2006.01) |

(52) U.S. Cl.
CPC .......... *A61K 9/0029* (2013.01); *A61K 31/175* (2013.01); *A61K 47/26* (2013.01)

(58) Field of Classification Search
CPC .... A61K 9/0029; A61K 31/175; A61K 47/26; A61K 9/08; A61K 9/0019
See application file for complete search history.

(56) References Cited

U.S. PATENT DOCUMENTS

| 5,403,858 | A | 4/1995 | Bastard et al. |
|---|---|---|---|
| 10,583,101 | B2 | 3/2020 | Gondaliya et al. |
| 2010/0068251 | A1 | 3/2010 | Ali et al. |
| 2016/0136116 | A1 | 5/2016 | Patel |
| 2019/0298671 | A1 | 10/2019 | Gondaliya et al. |

FOREIGN PATENT DOCUMENTS

| CN | 1110134 | 10/1995 | |
|---|---|---|---|
| CN | 1683016 | 10/2005 | |
| CN | 100998558 | 7/2007 | |
| CN | 101143130 | 3/2008 | |
| CN | 101444482 | 6/2009 | |
| CN | 100544710 | 9/2009 | |
| CN | 102198100 | 9/2011 | |
| CN | 103284957 | 9/2013 | |
| IN | 1909/MUM/2015 | 5/2017 | |
| JP | 05221852 | 8/1993 | |
| JP | HO8151333 | 6/1996 | |
| JP | 2009-509608 A * | 3/2009 | |
| JP | 2009509608 A * | 3/2009 | |
| WO | 2005072709 | 8/2005 | |
| WO | 2007036792 | 4/2007 | |
| WO | 2008119260 | 10/2008 | |
| WO | WO-2008119260 A1 * | 10/2008 | ............. A61K 31/17 |
| WO | 2010132664 | 11/2010 | |
| WO | 2018096466 | 5/2018 | |
| WO | 2019193477 | 10/2019 | |

OTHER PUBLICATIONS

Braun et al. European Journal of Pharmaceutics and Biopharmaceutics 94 (2015) 559-568 (Year: 2015).*
Kishore et al. (Pharm Res (2011) 28:1194-1210 (Year: 2011).*
ISO.org, Peroxide Value, SO 3960:2007(en) Animal and vegetable fats and oils—Determination of peroxide value—Iodometric (visual) endpoint determination, 2007 [retrieved on May 19, 2022]. Retrieved from the Internet <URL:https://www.iso.org/obp/ui/#iso:std:iso:3960:ed-4:v2:en>. (Year: 2007).*
Kumar et al. AAPS PharmSciTech 2006; 7, 3 (Year: 2006).*
SFPO. European Journal of Oncology Pharmacy, vol. 4, 2010/3 from URL: <https://sfpo.com/wp-content/uploads/2012/10/Recommandation_Stabilite_EJOP_2010_E3.pdf> Downloaded on Jun. 1, 2023. (Year: 2010).*
André, P., and F. Villain. "Free radical scavenging properties of mannitol and its role as a constituent of hyaluronic acid fillers: a literature review." International Journal of Cosmetic Science 39.4 (2017): 355-360. (Year: 2017).*
Takenaga, Mitsuko, "Application of Lipid Microspheres for the Treatment of Cancer" Advanced Drug Delivery Reviews, vol. 20, No. Jul. 2-3, 1996, pp. 209-219 (abstract only).
PCT International Search Report for PCT/IB2017/057328, dated Feb. 6, 2018.
PCT Search Strategy for PCT/IB2017/057328, dated Feb. 6, 2018.
PCT Written Opinion of the International Searching Authority for PCT/IB2017/057328, dated Feb 6. 2018.

(Continued)

*Primary Examiner* — Mina Haghighatian
*Assistant Examiner* — Janice Y Silverman
(74) *Attorney, Agent, or Firm* — Florek & Endres PLLC; Martin Endres

(57) ABSTRACT

The present invention relates to a ready-to-use solution of carmustine that does not require dissolution or dilution of the carmustine prior to addition to saline and dextrose parenteral solutions. In particular, the invention relates to a stable liquid pharmaceutical composition containing carmustine in the form of ready-to-use solution and method for preparing the same.

10 Claims, No Drawings

(56) References Cited

OTHER PUBLICATIONS

PCT International Search Report for PCT/IB2019/052644, dated Jun. 26, 2019.
PCT Search Strategy for PCT/IB2019/052644, dated Jun. 26, 2019.
PCT Written Opinion of the International Searching Authority for PCT/IB2019/052644, dated Jun. 26, 2019.
Kumari et al. "Nanosuspensions: A Review," International J. Pharm., 2017 7(2), 77-89.
Gossman et al., "Didodecyldimethylammonium Bromide (DMAB) Stabilized Poly(lactic-co-glycolic acid)(PLGA) Nanoparticles: Uptake and Cytotoxi Potential in Caco-2 Cells," Journal of Drug Delivery Science and Technology 43 (2018) 430-438 (available on line Nov. 6, 2017).
PCT International Search Report for PCT/IB2019/057404, dated Nov. 13, 2019.
PCT Search Strategy for PCT/IB2019/057404, dated Nov. 13, 2019.
PCT Written Opinion of the International Searching Authority for PCT/IB2019/057404, dated Nov. 13, 2019.
BiCNU (carmustine) for injections for intravenous use Package Insert Mar. 2017.
Indian Search Report for India Patent Application 202127009366 (Indian National Stage of PCT/IB2019/057404) dated Aug. 22, 2022.
European Search Report for European Patent Application No. 19858170 (European National Stage of PCT/IB2019/057404) dated Apr. 8, 2022.
Levin et al., "Dissolution and Stability of Carmustine in the Absence of Ethanol," Selective Cancer Therapeutics. Jan. 1989;5(1):33-53.
Vadlamudi et al., "Influence of Tween 80 on the Antileukemic Activity of 1,3-bis(2-(chloroethyl)-1-nitrosourea (nsc-409,962)," Arch Ital Pat Clin Tumori 1969; 12:163-175.
Braun et al., "Predicting Critical Micelle Concentration and Micelle Molecular Weight of Polysorbate 80 Using Compendial Methods," European Journal of Pharmaceutics and Biopharmaceutics. Aug. 1, 2015;94:559-68.
Kishore et al., "The Degradation of Polysorbates 20 and 80 and its Potential Impact on the Stability of Biotherapeutics," Pharmaceutical Research. Mar. 2011;28(5):1194-210.
ISO.org, Peroxide Value, SO 3960:2007(en) Animal and vegetable fats and oils—Determination of peroxide value—Iodometric (visual) endpoint determination, 2007 [retrieved on 2022-05-19]. Retrieved from the Internet <URL:https://www.iso.org/obp/ui/#iso:std:iso:3960:ed-4:v2:en>. (Year: 2007).
Kumar et al., "Removal of Peroxides in Polyethylene Glycols by Vacuum Drying: Implications in the Stability of Biotech and Pharmaceutical Formulations," Aaps Pharmscitech. Sep. 2006;7(3): E47-53.
Discloses liposome preparations and process for preparing the preparations by dissolving a fat-soluble medicine and a liposome matrix in an organic solvent to create a lipid-soluble liquor or dissolving the liposome matrix in an organic solvent to create a lipid-soluble liquor into an ampule, concurrently with a water-soluble liquid medicine and removing the organic solvent by vacuum drying.
Discloses a process for preparation carrier particles containing surface transferrin for glioma-targeted-chemotherapy. Biodegradable polymers like polylactic acid, polyglycolic acid, polycaprolactone or copolymer of lactic acid and glycolic acid and chemotherapeutic drugs such as carmustine, adriamycin or taxols are dissolved in acetone, acetonitrile or dimethyl sulfoxide; and the solution is emulsified in a solution of transferrin or combined wiith transferrin chemically after co-dialysis with cholesterol modified glucosan dialdehyde to prepare the drug-carrying polymer particle containing surface transferrin. Such particles may be injected into tumor cavity for targeted release of the drug.
Discloses a parenteral formulation of carmustine in the form of a stable oil-in-water emulsion. The composistion compromises of pharmaceutically effective amount of carmustine, oil, a surfactant and water for injection. The invention also discloses the method of preparation of the said oil-in-water emulsion.
Discloses sustained-release injectable formulations containing a nitrosourea drug, which comprises of sustained-release microspheres and solvents. The sustained-release microspheres each comprise an anticancer-active component selected from nitrosourea drugs (such as nimustine and carmustine) and/or topoisomerase inhibitors, and sustained-release agent. The solvents are common solvents or special solvents containing suspending agent.
Discloses a method for preparing an anticancer agent preparation by dissolving a fat-soluble anticancer agent in a medium chain or long chain fatty acid ester to form cores of lipid microspheres, adding a surfactant such as phospholipid to the core solution and subsequently homogenizing the mixture for coating the surfaces to produced lipid microspheres.
Discloses a liposome carmustine powder injection and a preparation process thereof.
Discloses carmustine compositsions.
Discloses a slow-release carmustine and fluoroacil composition.
Discloses a polylactic acid and carmustine microsphere.
Discloses a liposomal formulations of anti-cancer drugs.
Discloses carmustine, tween and co-solvent compositions.

\* cited by examiner

STABLE READY-TO-USE CARMUSTINE PHARMACEUTICAL COMPOSITION

The preset application is a continuation of U.S. patent application Ser. No. 17/268,022 filed Feb. 11, 2021 which is the U.S. National Stage filing of International Patent Application Number PCT/IB2019/057404, filed on Sep. 3, 20198, which claims the benefit of Indian Patent Applications No. 201821033221 Sep. 5, 2018, which are hereby incorporated by reference in its entirety.

FIELD OF THE INVENTION

The present invention relates to a ready-to-use solution of carmustine that does not require dissolution or dilution of the carmustine prior to addition to saline and dextrose parenteral solutions. In particular, the invention relates to a stable liquid pharmaceutical composition containing carmustine in the form of ready-to-use solution and method for preparing the same.

BACKGROUND OF THE INVENTION

Carmustine (bischloroethyl nitrosurea also known as BCNU) is a nitrosurea drug for the treatment of brain cancers owing to its ability to cross the blood-brain barrier and excellent activity against brain tumours.

Carmustine chemically known as 1,3-bis(2-chloroethyl)-1-nitrosourea (shown below) alkylates DNA, RNA and interferes with its synthesis and functions. It also binds and modifies (carbamoylates) glutathione reductase, which consequently leads to cell death.

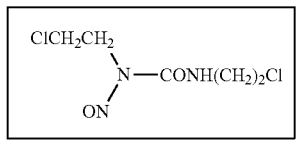

Carmustine is highly soluble in alcohol and lipids. Carmustine, however, is poorly soluble in water and is unstable in many formulations. For instance, carmustine gets readily hydrolyzed in water at pH>6. The solubility and stability issues of carmustine have been discussed previously. See, for example, Levin et al., *Selective Cancer Therapeutics*, 1989, 5(1), 33-35.

Though the drug has poor oral bioavailability, following IV infusion, it is rapidly taken up by the tissues, and due to its high lipid solubility, it can cross the blood brain barrier. However, it is rapidly degraded, with no unmetabolized drug detectable after 15 minutes.

Carmustine is commercially available as a lyophilized 100 mg powder for injection under the trade name BiCNU® in single dose vials. See the March 2017 prescribing information for BiCNU®, which is hereby incorporated by reference. Ethanol (dehydrated alcohol) (3 mL) is co-packaged with the drug product as a sterile diluent for reconstitution. To prepare the drug for administration, three preparation steps need to be performed. First, the lyophilized carmustine is reconstituted with the co-packed sterile dehydrated alcohol (3 mL) diluent. Second, the solution is further diluted with 27 mL of sterile water to form the reconstituted solution. Third, the reconstituted solution is further diluted with 5% Dextrose Injection, USP or Sodium Chloride Injection, USP (0.9% sodium chloride). This complicated preparation of carmustine solutions is time-consuming and can lead to errors in preparation and dosing.

The lyophilized formulation has several disadvantages including:
a) Extra handling, for example, due to the two step reconstitution;
b) In some cases, complete dissolution of the lyophilized powder may require prolonged shaking because of solubilisation problems;
c) Improper reconstitution of a lyophilized powder sometimes results in the formation of air-borne droplets ("blow-back"), which, in the case of a potent antitumor agent such as carmustine may be a health hazard to the personnel preparing the solution for injection;
d) Risk of improper dosing of a patient due to dilution with the wrong quantity of diluents; and and
e) The manufacturing of a lyophilized formulation is quite costly, since it not only requires capital investment for installation of a lyophilizer, but also its maintenance.

International patent application no. WO 2008/119260 discloses a pharmaceutical composition comprising a pharmaceutically effective amount of carmustine, Tween surfactant and a co-solvent selected from glycerol, polyethylene glycol, and a mixture thereof. The pharmaceutical composition may be in liquid form. Comparative example 2 of WO 2008/119260, which included carmustine, Tween 80, and 6 mL water for injection, was found to be less stable and failed to form a clear solution (turbidity) before freezing and freeze drying in 10 mL water for injection.

Indian patent application no. 1909/MUM/2015 discloses a ready-to-use injectable formulation which is free of surfactants.

There is an ongoing need for improved and simplified formulation of carmustine whose preparation and administration does not require either lyophilization or reconstitution. In particular, there is need for a stable, liquid, ready-to-use parenteral formulation of carmustine, which can be administered to a person in need thereof, without the hassles of reconstitution.

SUMMARY OF THE INVENTION

The present inventors while working on liquid, ready-to-use formulations of carmustine, surprisingly found that stable and clear solution of carmustine can be formulated with a suitable surfactant as the sole solvent. The present invention also provides a simple and cost-effective method of preparing a liquid, ready-to-use parenteral formulation of carmustine.

One embodiment of the invention is a liquid, ready-to-use parenteral pharmaceutical composition of carmustine.

Another embodiment is a liquid, ready-to-use parenteral pharmaceutical composition of carmustine dissolved in a suitable surfactant as the sole solvent.

The liquid, ready-to-use parenteral pharmaceutical composition of carmustine may have a concentration from about 2 mg/mL to about 500 mg/mL, preferably 100 mg/mL, 200 mg/mL or 300 mg/mL of carmustine.

The liquid, ready-to-use parenteral pharmaceutical composition of carmustine may be further admixed with 500 mL of 0.9% sodium chloride injection or 5% dextrose injection prior to actual clinical use.

One preferred embodiment is a liquid, ready-to-use parenteral pharmaceutical composition of 100 mg of carmustine dissolved in 1 mL of polysorbate (e.g., polysorbate 80) as the sole solvent. The pharmaceutical composition may be in a sealed vial. The polysorbate may be polysorbate 20, polysorbate 40, polysorbate 60, polysorbate 80 or any combination of any of the foregoing. In a preferred embodiment, the polysorbate is polysorbate 80, such as super refined polysorbate 80 (and more preferably polysorbate 80 with a peroxide value below 10 meq $O_2$/kg). In one embodiment, the peroxide value is about 0.5 meq $O_2$/kg. In yet another embodiment the peroxide value is about 0.2 meq $O_2$/kg.

Preferably, the pharmaceutical composition, after storage at 2-8° C. for 3 months, contains at least 90% by weight of the initial amount of carmustine. In one embodiment, the pharmaceutical composition is admixed with 500 mL of 0.9% sodium chloride injection or 5% dextrose injection to form an administrable solution prior to administration to a patient.

Yet another embodiment is a process for the preparation of a liquid, ready-to-use parenteral formulation of carmustine comprising:
  a) dissolving carmustine in a sufficient quantity of a suitable surfactant, for example, to achieve a concentration of 100 mg/ml;
  b) aseptic filtration (e.g., with a sterile 0.22 micron filter) of solution obtained in step (a) to obtain a sterile product, and
  c) filling the solution obtained in step (b) into a suitable container/closure system.
  d) optionally, inert gas purging (nitrogen) can be carried out during any of the steps.

Another embodiment is a method of preparing an administrable solution of carmustine comprising diluting the ready-to-use parenteral formulation of carmustine with an aqueous 0.9% sodium chloride solution (preferably Sodium Chloride Injection, USP) or an aqueous 5% dextrose solution (preferably 5% Dextrose Injection, USP) to obtain the administrable solution.

In one embodiment, the ready-to-use parenteral formulation of carmustine is diluted with 500 mL of an aqueous 0.9% sodium chloride solution (preferably Sodium Chloride Injection, USP) or 500 mL of an aqueous 5% dextrose solution (preferably 5% Dextrose Injection, USP).

In one preferred embodiment, the administrable solution has a pH in the range of 4 to 7 and an osmolality in the range of 330-390 mOsmol/L.

Yet another embodiment is a method of administering carmustine comprising intravenously administering an administrable carmustine solution as described herein to a patient in need thereof. The administrable carmustine solution may be prepared as described herein.

Yet another embodiment is a method for administering carmustine comprising:
  (a) adding a liquid, ready-to-use parenteral pharmaceutical composition of carmustine to 500 mL of 0.9% sodium chloride solution for injection or 5% dextrose solution for injection to form an administrable solution, wherein the pharmaceutical composition comprises, consists essentially of, or consists of 100 mg of carmustine dissolved in 1 mL of polysorbate 80 as the sole solvent, and
  (b) parenterally administering the administrable solution to a patient in need thereof.

In one embodiment, the ready-to-use pharmaceutical composition is stored at 2 to 8° C. in a sealed vial (such as, for example, 3, 6, 9, or 12 months) prior to being added to 0.9% sodium chloride solution for injection or 5% dextrose solution for injection.

Yet another embodiment is a method of treating cancer in a patient in need thereof by intravenously administering an administrable carmustine solution as described herein to the patient. The administrable carmustine solution may be prepared as described herein. The patient may be suffering from brain tumors glioblastoma, brainstem glioma, medulloblastoma, astrocytoma, ependymoma, metastatic brain tumors, multiple myeloma, relapsed or refractory Hodgkin's lymphoma, or relapsed or refractory Non-Hodgkin's lymphomas.

DETAILED DESCRIPTION OF THE INVENTION

The present invention relates to a stable, liquid pharmaceutical composition containing carmustine in the form of a ready-to-use solution and method for preparing the same.

As used herein, a "ready-to-use" or "RTU" composition is a sterile, liquid, injectable composition that is stable and has not been reconstituted from a lyophilizate.

Pharmaceutical Composition

One embodiment is a liquid, ready-to-use parenteral composition of carmustine dissolved in a suitable surfactant as the sole solvent.

The concentration of carmustine in the liquid, ready-to-use parenteral composition may vary from about 2 mg/mL to about 500 mg/mL, preferably 100 mg/mL, 200 mg/mL or 300 mg/mL.

Suitable surfactants include, but are not limited to, sodium salts of fatty alcohol sulphates, partial fatty acid esters of polyhydroxyethylene sorbitan such as polyoxyethylene sorbitan monolaurate (e.g., polyoxyethylene (20) sorbitan monolaurate, which is referred to as polysorbate 20 or Tween® 20), polyoxyethylene sorbitan monopalmitate (e.g., polyoxyethylene (20) sorbitan monopalmitate, which is referred to as polysorbate 40 or Tween® 40), polyoxyethylene sorbitan monostearate (e.g., polyoxyethylene (20) sorbitan monosterate, which is referred to as polysorbate 60 or Tween® 60), and polyoxyethylene sorbitan monooleate (e.g., polyoxyethylene (20) sorbitan monooleate, which is referred to as polysorbate 80 or Tween® 80), polyoxyethylene sorbitan tristearate (e.g., polyoxyethylene (20) sorbitan tristearate, which is referred to as polysorbate 65 or Tween® 65), and polyoxyethylene sorbitan trioleate (e.g., polyoxyethylene (20) sorbitan trioleate, which is referred to as polysorbate 85 or Tween® 85), polyoxyethylene glycol esters, polyoxyethylene castor oil derivatives, Cremophor® EL (PEG-35 castor oil), Cremophor® RH40 (PEG-40 hydrogenated castor oil), polyoxyethylene 15 hydroxystearate, polyoxyethylene alkyl ethers (sold under the tradename Brij®); polyoxyethylene stearates (Myrj®), sorbitan derivatives, fatty acid esters of sorbitan, poloxamers (e.g., poloxamer 188, poloxamer 407, poloxamer 338, and poloxamer 184), poloxamine (e.g., poloxamine 304, poloxamine 904, and poloxamine 908), lecithin, an ethoxylated vegetable oil, vitamin E tocopherol propylene glycol succinate (vitamin E-TPGS), polyoxyethylene-polyoxypropylene block copolymers, incrocas 35, TPGS (D-α-tocopherol polyethylene glycol 1000 succinate), tyloxapol, sodium oleate, sodium deoxycholate and mixtures thereof.

In one preferred embodiment, the surfactant is selected from various grades of polysorbate, such as polysorbate 20, polysorbate 40, polysorbate 60, polysorbate 80 and mixtures thereof. More preferably, the surfactant is polysorbate (e.g., super refined polysorbate 80) with a peroxide value below 10 meq $O_2$/kg. In one embodiment, the peroxide value is about 0.5 meq $O_2$/kg. In yet another embodiment the peroxide value is about 0.2 meq $O_2$/kg.

According to one preferred embodiment, 100 mg of carmustine is dissolved in a sufficient quantity of surfactant (up to 1 mL to make up the final volume). In one embodiment, the fill volumes of RTU liquid may be 1 mL or 3 mL.

The pharmaceutical composition may optionally include other optional pharmaceutical excipients such as antioxidants. Suitable antioxidants include, but are not limited to, acetone sodium bisulfite, argon, ascorbyl palmitate, ascorbic acid, sodium bisulfite, butylated hydroxy anisole (BHA), butylated hydroxy toluene (BHT), citric acid, cystein/cysteinate HCl, acetylcystein, dithionite sodium (Na hydrosulfite, Na sulfoxylate), gentisic acid, gentisic acid, ethanolamine, glutamate monosodium, glutathione, formaldehyde sulfoxylate sodium, metabisulfite sodium, metabisulfite potassium, methionine, monothioglycerol (thioglycerol), sulfite sodium, tocopherols alpha, alpha tocopherol hydrogen succinate, thioglycolate sodium, sodium formaldehyde sulfoxylate, thiourea, and any combination of any of the foregoing.

The concentration of antioxidant may range between 0.001 mg/mL to 5 mg/mL.

In one embodiment, the pharmaceutical composition, after storage at 2-8° C. for 3, 6, 9, or 12 months, contains at least 90, 92, 94, 95, 96, 97, or 98% by weight of the initial amount of carmustine. In another embodiment, the pharmaceutical composition, after storage at 2-8° C. for 3, 6, 9, or 12 months, contains at least 90% by weight of the initial amount of carmustine.

Process of Preparation for the RTU Composition

The liquid, ready-to-use parenteral composition of carmustine may be prepared by:
 a) dissolving carmustine in a sufficient quantity of a suitable surfactant (e.g., to achieve 100 mg/mL concentration),
 b) aseptic filtration (e.g., with a sterile 0.22 micron filter) of the carmustine solution obtained in step (a) to obtain a sterile product, and
 c) filling the solution obtained in step (b) into a suitable container/closure system Optionally, purging inert gas (nitrogen) during any of the aforementioned steps.

The liquid, ready-to-use parenteral formulation of carmustine may be a clear, pale yellow and free from visible particles.

In one embodiment, the stable liquid, ready-to-use parenteral formulation of carmustine of present invention has a concentration of about 100 mg/mL of carmustine.

This liquid, ready-to-use parenteral formulation of carmustine can be filled in a suitable container/closure system, e.g., ampoules, vials, and prefilled syringe system. The ready-to-use solution may be stored in an amber type-I glass vial or polypropylene container (such as a polypropylene container which is polyvinyl chloride (PVC) free and di-2-ethylhexy phthalate (DEHP) free). These solutions are preferably not stored in a polyvinyl chloride container. In one embodiment, the head space of each vial contains no more than 6.0% by volume oxygen.

The liquid, ready-to-use parenteral formulation of carmustine may have a pH in the range of 4-7.

Prior to administration, the liquid, ready-to-use parenteral composition of carmustine may be further admixed with 0.9% sodium chloride injection (e.g., Sodium Chloride Injection, USP) or 5% dextrose injection (e.g., 5% Dextrose Injection, USP) to form an administrable solution. For instance, in one embodiment, the ready-to-use composition is further admixed with 500 mL of 0.9% sodium chloride injection or 5% dextrose injection.

The U.S. Pharmacopeia, USP 42-NF 37 (2019) is hereby incorporated by reference, including the entries for Sodium Chloride Injection, USP and 5% Dextrose Injection, USP.

The administrable solution may be a faint yellow colour with a pH in the range of 4 to 7 and osmolality in the range of 330-390 mOsmol/L.

The administrable solution may be stored in a glass or polypropylene container (such as a polypropylene container which is polyvinyl chloride (PVC) free and di-2-ethylhexy phthalate (DEHP) free). These solutions are preferably not stored in a polyvinyl chloride container.

The administrable carmustine solution can have a concentration of about 0.2 mg/mL of carmustine As used herein, a "stable" composition means no aggregation observed when stored at conventional storage conditions like 2° C. to 8° C. (long term) for appropriate time and wherein the assay of carmustine is not less than 90% (based on 100% initial carmustine).

The carmustine content may be determined by methods known in the art, such as high performance liquid chromatography (HPLC method), and spectrophotometry (UV spectrophotometry). HPLC was used for performing the carmustine assay studies described herein.

Based on the results of table 2, it was concluded that the liquid, ready-to-use parenteral formulation of carmustine of the present invention, was stable for up to 3 months when stored at 2° C.-8° C.

Administration

The carmustine administrable solution may be administered by slow intravenous infusion over at least two hours. In one embodiment, the injected area is monitored during the administration. In another embodiment, the rate of administration of the intravenous infusion is no more than 1.66 mg/m$^2$/min.

The carmustine administrable solution may be administered to a patient to treat brain tumors glioblastoma, brainstem glioma, medulloblastoma, astrocytoma, ependymoma, metastatic brain tumors, multiple myeloma, relapsed or refractory Hodgkin's lymphoma, or relapsed or refractory Non-Hodgkin's lymphomas.

In one embodiment, the carmustine administrable solution is administered to a patient as a single agent or in a combination therapy (such as with other chemotherapeutic agents) to treat (i) brain tumors glioblastoma, brainstem glioma, medulloblastoma, astrocytoma, ependymoma, or metastatic brain tumors, (ii) multiple myeloma in combination with prednisone, (iii) relapsed or refractory Hodgkin's lymphoma in combination with other approved drugs (such as chemotherapeutic agents), or (iv) relapsed or refractory Non-Hodgkin's lymphomas in combination with other approved drugs (such as chemotherapeutic agents).

The carmustine administrable solution may be administered as a single agent in previously untreated patients at a dose of 150 to 200 mg/m$^2$ carmustine intravenously every 6 weeks. The carmustine administrable solution may be administered as a single dose or divided into daily injections such as 75 to 100 mg/m$^2$ on two successive days. The dose may be lowered when the carmustine administrable solution is used with other myelosuppressive drugs or in patients in whom bone marrow reserve is depleted. The carmustine administrable solution may be administered for the duration according to the established regimen. In one embodiment, the patient is premedicated before each dose with antiemetics.

The dosing (after the initial dose) may be adjusted according to the hematologic response of the patient to the preceding dose. In one embodiment, the patient is dosed as follows:

| Nadir After Prior Dose | | Percentage of Prior Dose to be Given |
|---|---|---|
| Leukocytes/mm³ | Platelets/mm³ | |
| >4000 | >100,000 | 100% |
| 3000-3999 | 75,000-99,999 | 100% |
| 2000-2999 | 25,000-74,999 | 70% |
| <2000 | <25,000 | 50% |

The hematologic toxicity can be delayed and cumulative. In one embodiment, the patient's blood counts are monitored weekly. In another embodiment, a repeat course of the carmustine administrable solution is not administered until circulating blood elements have returned to acceptable levels (platelets above 100 Gi/L, leukocytes above 4 Gi/L and absolute neutrophil count above 1 Gi/L). In yet another embodiment, the interval between courses is 6 weeks.

In yet another embodiment, renal function is evaluated prior to administration and/or periodically during treatment. In one embodiment, carmustine treatment is discontinued if the creatinine clearance is less than 10 mL/min. In another embodiment, carmustine is not administered to patients with compromised renal function. In yet another embodiment, transaminases and bilirubin are monitored periodically during treatment.

The following examples further illustrate the invention but should not be construed as in any way limiting its scope. In particular, the processing conditions are merely exemplary and can be varied by one of ordinary skill in the art.

All patents and other references cited herein are hereby incorporated by reference in their entireties

EXAMPLES

Example 1

TABLE 1

| Composition of liquid, ready-to-use parenteral formulations of carmustine | |
|---|---|
| Composition | Formulation 1 |
| Carmustine | 100 mg |
| Polysorbate 80 NF | q.s to 1 mL |

(a) 100 mg of carmustine was dissolved in sufficient quantity (q.s. to 1 mL) of polysorbate 80 NF surfactant, under inert (nitrogen) gas purging.
(b) The solution obtained in step (a) was aseptically filtered (sterile 0.22 micron filter) under inert (nitrogen) gas purging to obtain a sterile product.
(c) The solution obtained in step (b) was filled into a sterile amber coloured type-I glass vial.

The stability of the formulation was tested after 3 months of storage at 2-8° C. The results are provided in Table 2 below.

TABLE 2

Evaluation of liquid ready-to-use parenteral formulations of carmustine

| | Stability data | |
|---|---|---|
| Test | Initial | 3 months (2° C.-8° C.) |
| Description | Clear pale yellow color solution | Clear pale yellow color solution |
| Assay | 101.50% | 97.21% |
| Related substances | | |
| Impurity A* | 0.20% | 1.80% |
| Any unspecified impurity | BLD** | BLD** |
| Total impurities | 0.20% | 1.80% |

*Impurity A refers to 1,3-bis(2-chloroethyl)urea
*BLD: below limit of detection

We claim:

1. A method of administering carmustine to a patient consisting of:
   (i) providing a carmustine solution consisting of: (a) about 100 mg/mL to about 500 mg/mL of carmustine; and (b) a super refined polysorbate with a peroxide value below 10 meq $O_2$/kg to a person administering carmustine to the patient wherein the carmustine solution has not been reconstituted from a lyophilizate and the carmustine solution is provided in a sealed container that is free of polyvinyl chloride and free of di-2-ethylhexylphthalate;
   (ii) adding the carmustine solution of step (i) directly to 500 ml of a 0.9% sodium chloride injection solution or 500 ml of a 5% dextrose injection solution to form an administrable solution without any prior dissolution or prior dilution of the carmustine solution; and
   (iii) parenterally administering the administrable solution of step (ii) to the patient.

2. The method according to claim 1, wherein the polysorbate is selected from polysorbate 20, polysorbate 40, polysorbate 60, polysorbate 80 and mixtures thereof.

3. The method according to claim 1, wherein the polysorbate is super refined polysorbate 80.

4. The method according to claim 1, wherein the administrable solution has a concentration of about 0.2 mg/mL of carmustine.

5. The method according to claim 1, wherein the polysorbate is super refined polysorbate with a peroxide value about 0.2 meq $O_2$/kg to about 0.5 meq $O_2$/kg.

6. The method according to claim 5, wherein the polysorbate is super refined polysorbate with a peroxide value about 0.5 meq $O_2$/kg.

7. The method according to claim 5, wherein the polysorbate is super refined polysorbate with a peroxide value about 0.2 meq $O_2$/kg.

8. The method according to claim 1 wherein the carmustine solution is stored in the container with a head space within the container comprising not more than 6% oxygen.

9. The method according to claim 8 wherein after the carmustine solution is stored at 2° C. to 8° C. for 3 months in the sealed container the carmustine solution contains at least 90% by weight of the initial amount of carmustine and is free of visible particles.

10. The method according to claim 8 wherein after the carmustine solution is stored at 2° C. to 8° C. for 3 months in the sealed container the carmustine solution contains at least 95% by weight of the initial amount of carmustine and is free of visible particles.

\* \* \* \* \*